US012585877B2

(12) United States Patent
Gashteovski et al.

(10) Patent No.: US 12,585,877 B2
(45) Date of Patent: Mar. 24, 2026

(54) GROUPING AND LINKING FACTS FROM TEXT TO REMOVE AMBIGUITY USING KNOWLEDGE GRAPHS

(71) Applicant: NEC Laboratories Europe GmbH, Heidelberg (DE)

(72) Inventors: Kiril Gashteovski, Heidelberg (DE); Gorjan Radevski, Heidelberg (DE); Carolin Lawrence, Heidelberg (DE); Goran Glavas, Wuerzburg (DE)

(73) Assignee: NEC CORPORATION, Tokyo (JP)

( * ) Notice: Subject to any disclaimer, the term of this patent is extended or adjusted under 35 U.S.C. 154(b) by 329 days.

(21) Appl. No.: 18/317,953

(22) Filed: May 16, 2023

(65) Prior Publication Data

US 2024/0296285 A1    Sep. 5, 2024

Related U.S. Application Data

(60) Provisional application No. 63/449,609, filed on Mar. 3, 2023.

(51) Int. Cl.
*G06F 40/284* (2020.01)
*G06F 40/20* (2020.01)
(Continued)

(52) U.S. Cl.
CPC ............ *G06F 40/284* (2020.01); *G06F 40/20* (2020.01); *G06F 40/279* (2020.01); *G06F 40/30* (2020.01);
(Continued)

(58) Field of Classification Search
None
See application file for complete search history.

(56) References Cited

U.S. PATENT DOCUMENTS 9,965,726 B1    5/2018  Tablan et al.
12,099,955 B2 *  9/2024  Goel ................ G06Q 10/06375
(Continued)

FOREIGN PATENT DOCUMENTS

CN      113377930 B    11/2021
CN      115858811 A  *  3/2023
(Continued)

OTHER PUBLICATIONS

Fengyuan Lu , Peijin Cong, Xinli Huang; Utilizing Textual Information in Knowledge Graph Embedding: A Survey of Methods and Applications; May 2, 2020; URL: https://ieeexplore.ieee.org/stamp/stamp.jsp?tp=&arnumber=9094215&tag=1 (Year: 2020).*
(Continued)

*Primary Examiner* — Richa Sonifrank
(74) *Attorney, Agent, or Firm* — Leydig, Voit & Mayer, Ltd.

(57)    ABSTRACT

A method for disambiguating textual facts by linking the textual facts to a reference knowledge graph and introducing entities and relations for the textual facts includes ranking the textual facts from textual data. Each of the textual facts is in a triple data structure comprising a subject, a relation, and an object. The method further includes determining whether each element of the triple data structure should be linked to an existing entry within the reference knowledge graph or become a new entry within the data element, and generating an enriched knowledge graph based on the determination. A ranking module using machine learning can be used. The method can help users for decision making and can be used in a variety of applications including, but not limited to, several use cases in drug development, material synthesis, inventory of items, detection of suspects from textual messages, and medical/healthcare.

17 Claims, 5 Drawing Sheets

100

(51) Int. Cl.

| | |
|---|---|
| *G06F 40/279* | (2020.01) |
| *G06F 40/30* | (2020.01) |
| *G06F 40/40* | (2020.01) |
| *G06N 3/042* | (2023.01) |
| *G06N 3/045* | (2023.01) |
| *G06N 3/048* | (2023.01) |
| *G06N 3/08* | (2023.01) |
| *G06N 3/09* | (2023.01) |
| *G06N 5/02* | (2023.01) |
| *G06N 5/022* | (2023.01) |
| *G06N 20/00* | (2019.01) |
| *G16H 70/40* | (2018.01) |

(52) U.S. Cl.
CPC ............. *G06F 40/40* (2020.01); *G06N 3/042* (2023.01); *G06N 3/045* (2023.01); *G06N 3/048* (2023.01); *G06N 3/08* (2013.01); *G06N 3/09* (2023.01); *G06N 5/02* (2013.01); *G06N 5/022* (2013.01); *G06N 20/00* (2019.01); *G16H 70/40* (2018.01)

(56) References Cited

U.S. PATENT DOCUMENTS

| | | | | |
|---|---|---|---|---|
| 12,455,915 | B2 * | 10/2025 | Saha | G06F 40/279 |
| 2017/0024375 | A1 | 1/2017 | Hakkani-Tur et al. | |
| 2018/0197104 | A1 * | 7/2018 | Marin | G06N 5/022 |
| 2019/0034780 | A1 * | 1/2019 | Marin | G06F 16/3329 |
| 2019/0122111 | A1 * | 4/2019 | Min | G06N 3/048 |
| 2019/0236469 | A1 * | 8/2019 | Canim | G06N 5/045 |
| 2019/0303857 | A1 * | 10/2019 | Lecue | G06F 16/29 |
| 2019/0392330 | A1 * | 12/2019 | Martineau | G06N 5/04 |
| 2020/0089766 | A1 * | 3/2020 | Lassoued | G06F 40/30 |
| 2020/0160149 | A1 * | 5/2020 | Morita | G06N 3/09 |
| 2021/0117815 | A1 * | 4/2021 | Creed | G06N 20/00 |
| 2021/0216580 | A1 * | 7/2021 | Liu | G06F 16/355 |
| 2022/0188895 | A1 * | 6/2022 | Lipka | G06N 5/04 |
| 2022/0222442 | A1 | 7/2022 | Akimoto et al. | |
| 2022/0230625 | A1 * | 7/2022 | Zhu | G06F 18/2155 |
| 2022/0253477 | A1 * | 8/2022 | Lipka | G06N 20/00 |
| 2022/0366274 | A1 * | 11/2022 | Lawrence | G06N 20/00 |
| 2022/0398271 | A1 | 12/2022 | Wu et al. | |
| 2023/0039937 | A1 * | 2/2023 | Wendell | G06F 16/9024 |
| 2023/0169270 | A1 | 6/2023 | Wang | |
| 2023/0237271 | A1 * | 7/2023 | Ferrucci | G16H 70/60 707/726 |
| 2023/0267341 | A1 * | 8/2023 | Stepanova | G06F 40/30 706/61 |
| 2023/0289618 | A1 * | 9/2023 | Takahashi | G06N 3/045 |
| 2023/0324878 | A1 * | 10/2023 | Ishii | G05B 19/4083 700/52 |
| 2024/0112044 | A1 * | 4/2024 | Kim | G06N 5/022 |
| 2024/0273294 | A1 * | 8/2024 | Shakeri | G06F 40/295 |

FOREIGN PATENT DOCUMENTS

| | | | | | |
|---|---|---|---|---|---|
| WO | 2020/240871 | A1 | 12/2020 | | |
| WO | WO-2021139101 | A1 * | 7/2021 | ............. | G06N 20/00 |
| WO | WO 2021/178750 | A1 | 9/2021 | | |
| WO | WO 2021/179897 | A1 | 9/2021 | | |
| WO | WO-2022174356 | A1 * | 8/2022 | ........... | G06F 16/243 |

OTHER PUBLICATIONS

Robert L. Logan IV, Nelson F. Liu, Matthew E. Peters, Matt Gardner, Sameer Singh; Barack's Wife Hillary: Using Knowledge-Graphs for Fact-Aware Language Modeling; Jun. 20, 2020; URL: https://arxiv.org/pdf/1906.07241 (Year: 2020).*

Hermann Kroll; Jan Pirklbauer; Wolf-Tilo Balke; A Toolbox for the Nearly-Unsupervised Construction of Digital Library Knowledge Graphs; Sep. 30, 2021; URL: https://ieeexplore.ieee.org/stamp/stamp.jsp?tp=&arnumber=9651799 (Year: 2021).*

Peng Liu; Feng Chen; Jing Ma; Jiahao Zhang; Research on Prediction of Link Embedding in Maritime Knowledge Graph Dec. 29, 2021; URL https://ieeexplore.ieee.org/stamp/stamp.jsp?tp=&arnumber=9742040 (Year: 2021).*

Liang Yao, Chengsheng Mao, Yuan Luo; KG-BERT: BERT for Knowledge Graph Completion; Sep. 11, 2019; URL: https://arxiv.org/pdf/1909.03193 (Year: 2019).*

Benno Kruit, Peter Boncz, and Jacopo Urbani; Extracting Novel Facts from Tables for Knowledge Graph Completion; Oct. 17, 2019; URL: https://link.springer.com/chapter/10.1007/978-3-030-30793-6_21 (Year: 2019).*

De Cao, Nicola et al.; "Autoregressive Entity Retrieval"; *International Conference on Learning Representations*; Mar. 24, 2021; pp. 1-20; vol. 3; ArXiv.org, Cornell University; Ithaca, NY, USA.

Gao, Silin et al.; "ComFact: A Benchmark for Linking Contextual Commonsense Knowledge"; 2022 *Conference on Empirical Methods in Natural Language Processing*; Oct. 23, 2022; pp. 1-20; ArXiv.org, Cornell University; Ithaca, NY, USA.

Jiang, Zhengbao et al.; "CoRI: Collective Relation Integration with Data Augmentation for Open Information Extraction"; *Proceedings of the 59th Annual Meeting of the Association for Computational Linguistics and the 11th International Joint Conference on Natural Language Processing*; pp. 4706-4716; vol. 1; Association for Computational Linguistics, MIT Press; Cambridge, MA, USA.

Johnson, Jeff et al.; "Billion-scale Similarity Search with GPUs"; *IEEE Transactions on Big Data*; Feb. 28, 2017; pp. 1-20; vol. 1; IEEE; Piscataway, NJ, USA.

Piskorski, Jakub et al.; "Information Extraction: Past, Present and Future"; *Multi-source, Multilingual Information Extraction and Summarization 11—Theory and Applications of Natural Language Processing—Chapter 2*; Aug. 1, 2012; pp. 23-49; ISBN: 978-3-642-28568-4; Springer-Verlag; Berlin, Heidelberg, Germany.

Singh, Sonit; "Natural Language Processing for Information Extraction"; *Computer Science*; Jul. 6, 2018; pp. 1-24; ArXiv.org, Cornell University; Ithaca, NY, USA.

Van Den Oord, Aaron et al.; " Representation Learning with Contrastive Predictive Coding"; *Machine Learning*; Jan. 22, 2019; pp. 1-13; vol. 2; ArXiv.org, Cornell University; Ithaca, NY, USA.

Wood, Ian David et al.; "Integrating Lexical Information into Entity Neighbourhood Representations for Relation Prediction"; *Proceedings of the 2021 Conference of the North American Chapter of the Association for Computational Linguistics: Human Language Technologies*; Jun. 6-11, 2021; pp. 3429-3436; Association for Computational Linguistics; Stroudsburg, PA, USA.

Wu, Ledell et al.; "Scalable Zero-shot Entity Linking with Dense Entity Retrieval"; 2020 *Conference on Empirical Methods in Natural Language Processing*; Sep. 29, 2020; pp. 1-11; vol. 3; ArXiv.org, Cornell University; Ithaca, NY, USA.

Zhang, Dongxu et al.; "OpenKI: Integrating Open Information Extraction and Knowledge Bases with Relation Inference"; *Proceedings of the 2019 Conference of the North American Chapter of the Association for Computational Linguistics: Human Language Technologies*; Jun. 2-7, 2019; pp. 762-772; vol. 1; Association for Computational Linguistics, MIT Press; Cambridge, MA, USA.

* cited by examiner

100

200

300

400

GROUPING AND LINKING FACTS FROM TEXT TO REMOVE AMBIGUITY USING KNOWLEDGE GRAPHS

CROSS-REFERENCE TO PRIOR APPLICATION

Priority is claimed to U.S. Provisional Application No. 63/449,609, filed on Mar. 3, 2023, the entire contents of which is hereby incorporated by reference herein.

FIELD

The present invention relates to a method, system and computer-readable medium for grouping and linking facts from text to remove ambiguity using knowledge graphs.

BACKGROUND

A user can be provided with vast amounts of textual information that includes a plurality of facts within the text. A process can be used to assist the user (e.g., help humans) reduce the cognitive load by highlighting facts from texts in the form of triples, which can take the shape of ("subject", "relation", "object"). The subject and object can be entities in the world and the relation can describe a relationship between the subject and object. However, both entities and relations can be ambiguous. For example, both "cytotoxic T cell" and "CTL" can be used to refer to the same entity. In other examples, the term "CTL" can refer to a cutlet. This is especially true across different documents, and therefore, it is difficult linking entities or relations that might mean the same, but have different surface text strings. However, if such linking is not performed, then users might miss out on crucial information.

SUMMARY

In an embodiment, the present disclosure provides a method for disambiguating textual facts by linking the textual facts to a reference knowledge graph and introducing entities and relations for the textual facts. The textual facts from textual data are ranked, and each of the textual facts is in a triple data structure comprising a subject, a relation, and an object. A determination is performed as to whether each element of the triple data structure of the textual facts should be linked to an existing entry within the reference knowledge graph or whether the element should become a new entry within the data element. An enriched knowledge graph is generated based on the determination.

BRIEF DESCRIPTION OF THE DRAWINGS

Embodiments of the present invention will be described in even greater detail below based on the exemplary figures. The present invention is not limited to the exemplary embodiments. All features described and/or illustrated herein can be used alone or combined in different combinations in embodiments of the present invention. The features and advantages of various embodiments of the present invention will become apparent by reading the following detailed description with reference to the attached drawings which illustrate the following.

DETAILED DESCRIPTION

Figure 1:
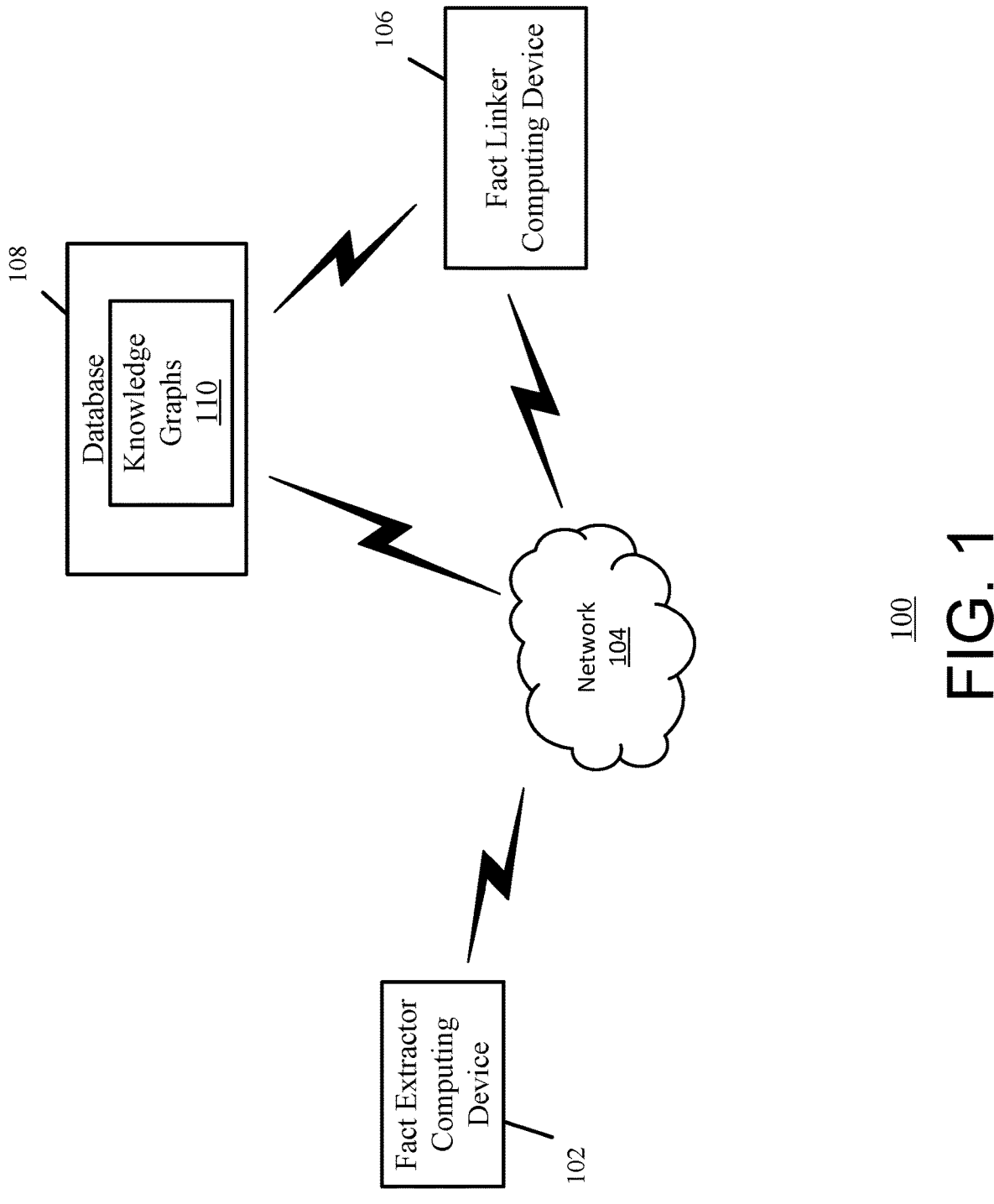
FIG. 1 illustrates a simplified block diagram depicting an exemplary computing environment according to an embodiment of the present disclosure.

Embodiments of the present invention receive an input in the form of textual facts in the form of (subject, relation, object)-triples, which were previously extracted with a fact extractor. Then, for each slot of the textual fact (e.g., for each subject, relation, and/or object), embodiments of the present invention (1) rank all knowledge graph counter-parts from the most probable to least probable (e.g., embodiments of the present invention can link the slots of the textual fact to knowledge graph entries); and/or (2) determine whether the most probable knowledge graph counter-part is actually correct (e.g., embodiments of the present invention classifies whether the slot is in the knowledge graph or not). In addition, embodiments of the present invention add the newly linked fact to the knowledge graph. Among other advantages, embodiments of the present invention provide technical improvements over the prior art by linking both entities and relations to a large scale KG, and implement a tailor-made module for dealing with polysemous entities. Embodiments of the present invention can be used for numerous practical applications that are described below including, but not limited to, discovering new canonical facts from text data that contain information about using a particular drug to treat a particular patient, a list of linked facts for discovering items and locations of items within a facility based on extracting and/or linking the extracted information about the stored items in a facility, and/or a list of linked facts to reduce the time and costs of errors in the wet-lab costs of material design.

Given vast amounts of textual information, the cognitive load for humans (e.g., users) can be helped by highlighting facts from texts in the form of triples that take the shape ("subject", "relation", "object"), where subject and object are entities in the world. However, both entities and relations can be ambiguous. For example, both "cytotoxic T cell" and the term "CTL" can be used to refer to the same entity. Other times, the term "CTL" can refer to a cutlet. Especially across different documents, it is therefore difficult to link entities or relations that mean the same (e.g., have the same meaning), but have different surface strings. However, if such linking is not done (e.g., performed), then humans might miss out on crucial information. Embodiments of the present invention can perform this kind of linking, which can aid humans to comprehend vast amount of text by linking information across documents in an easy to digest manner. To solve this, the below challenges are tackled in embodiments of the present invention.

For instance, first, how can an entity or relation be linked to a concise concept, such as an entry in a knowledge graph? In an example: ("CD8 T cells", "play a crucial role in", "immunity") during training, and ("cytotoxic T cell", "is a", "cell type") during inference.

Second, how can it be recognized that a particular entity or relation does not yet have a concept in a knowledge graph? In an example: ("CD8 T cells", "play a crucial role in", "cancer immunity") the model does not encounter "cancer immunity" or "CD8 T Cells" during training.

Third, how can entities be disambiguated with the same name? In an example: ("CTL", "play a crucial role in", "cancer immunity"), ("CTL", "converts coal into", "liquid hydrocarbons"), where the first occurrence of CTL is a cell, while the second occurrence of CTL is an engineering process of coal liquefaction. Therefore, context is necessary to disambiguate which CTL entity is the correct one: a cell or an engineering process.

According to a first aspect, the present disclosure provides a method for disambiguating textual facts by linking the textual facts to a reference knowledge graph and introducing entities and relations for the textual facts. The textual facts from textual data are ranked and each of the textual facts is in a triple data structure comprising a subject, a relation, and an object. The method further includes determining whether each element of the triple data structure of the textual facts should be linked to an existing entry within the reference knowledge graph or whether the element should become a new entry within the data element, and generating an enriched knowledge graph based on the determination.

According to a second aspect, the method according to the first aspect further comprises obtaining the textual data of interest, and using a fact extractor on the textual data of interest to generate the textual facts. The subject and the object are entities.

According to a third aspect, the method according to the first or the second aspect further comprises setting up the reference knowledge graph comprising a set of entities, a set of relations, and a set of knowledge graph facts.

According to a fourth aspect, the method according to the third aspect further comprises that the reference knowledge graph starts with empty sets for the set of entities, the set of relations, and the set of knowledge graph facts.

According to a fifth aspect, the method according to the third aspect further comprises that setting up the reference knowledge graph comprises: determining whether one or more previous facts from previous textual data exists in the reference knowledge graph, and based on determining that the one or more previous facts does not exist in the reference knowledge graph, adding new entity and relations associated with the one or more previous facts as well as the one or more previous facts into the reference knowledge graph.

According to a sixth aspect, the method according to any of the first to fifth aspects further comprises inputting the enriched knowledge graph into a knowledge graph predictor to determine a final outcome.

According to a seventh aspect, the method according to the sixth aspect further comprises that the textual data indicates textbooks and publications, and wherein the final outcome indicates information associated with using a particular drug to treat a particular patient.

According to an eighth aspect, the method according to the sixth aspect further comprises that the textual data indicates facility reports and/or logs indicating stored items in a facility, and the final outcome indicates linked facts indicating items and robots in an inventory and locations of the items and the robots within the facility. The method further comprises operating an artificial intelligence (AI) system to command the robots in the facility to move the items to a proper location based on the final outcome.

According to an ninth aspect, the method according to any of the first through eighth aspects further comprising that ranking the textual facts from the textual data comprises: determining textual fact embeddings for the textual facts based on using a first pre-trained language model (LM), determining knowledge graph embeddings for the reference knowledge graph based on using a second pre-trained LM, and ranking the textual facts based on the knowledge graph embeddings and the textual fact embeddings.

According to an tenth aspect, the method according to the ninth aspect further comprising that determining the knowledge graph embeddings for the reference knowledge graph comprises: determining one or more knowledge graph entity and relation embedding vectors using frozen knowledge graph embeddings, determining one or more intermediate knowledge graph embeddings using the second pre-trained LM, and determining the knowledge graph embeddings based on using an aggregator, the one or more knowledge graph entity and relation embedding vectors, and the one or more intermediate knowledge graph embeddings.

According to an eleventh aspect, the method according to the ninth aspect further comprising that ranking the textual facts based on the knowledge graph embeddings and the textual fact embeddings comprises using a shared latent space between the knowledge graph embeddings and the textual fact embeddings to rank the textual facts.

According to an twelfth aspect, the method according to any of the first through eleventh aspects further comprising that determining whether each element of the triple data structure of the textual facts should be linked to the existing entry within the reference knowledge graph or whether the element should become the new entry within the data element comprises: generating one or more aggregated feature vectors for each of the textual facts, determining one or more probability scores for each of the textual facts based on the one or more aggregated feature vectors, and determining whether each element of the triple data structure of the textual facts should be linked to the existing entry within the reference knowledge graph or whether the element should become the new entry within the data element based on comparing the one or more probability scores with a threshold.

According to a thirteenth aspect, the method according to any of the first through twelfth aspects further comprising that the one or more aggregated feature vectors comprise a ranking score, a previous link, a current link, a current link additional information, and a closest text. Further, determining the one or more probability scores is based on using a softmax layer in a neural network.

According to a fourteenth aspect of the present disclosure, a system for disambiguating textual facts by linking the textual facts to a reference knowledge graph and introducing entities and relations for the textual facts is provided, the system comprising one or more hardware processors, which, alone or in combination, are configured to provide for execution of the following steps: ranking the textual facts from textual data, determining whether each element of the triple data structure of the textual facts should be linked to an existing entry within the reference knowledge graph or whether the element should become a new entry within the data element, and generating an enriched knowledge graph based on the determination. Each of the textual facts is in a triple data structure comprising a subject, a relation, and an object.

A fifteenth aspect of the present disclosure provides a tangible, non-transitory computer-readable medium having instructions thereon, which, upon being executed by one or more processors, provides for execution of the method according to any of the first to the thirteenth aspects.

FIG. 1 illustrates a simplified block diagram depicting an exemplary computing system according to an embodiment of the present disclosure. For instance, FIG. 1 shows a computing system 100 comprising a fact extractor computing device 102, a network 104, a fact linker computing device 106, and a database 108. The database 108 includes one or more knowledge graphs (KG) 110. Although certain entities within system 100 are described below and/or depicted in the FIGS. as being singular entities, it will be appreciated that the entities and functionalities discussed herein can be implemented by and/or include one or more entities. For example, in some instances, the fact linker computing device 104 can be and/or include multiple computing devices such as a first computing device that is configured to perform ranking (e.g., using a ranking module, engine, or processor) and a second computing device that is configured to perform linking (e.g., using a linking module, engine, or processor).

The entities within the system 100 are in communication with other devices and/or systems within the system 100 via the network 104. The network 104 can be a global area network (GAN) such as the Internet, a wide area network (WAN), a local area network (LAN), or any other type of network or combination of networks. The network 104 can provide a wireline, wireless, or a combination of wireline and wireless communication between the entities within the system 100.

The fact extractor computing device 102 is a computing device that is configured to extract facts from text (e.g., textual information and/or textual documents). For example, as will be explained below, the fact extractor computing device 102 is configured to determine facts, which can be in a form of a triple such as "subject", "relation", "object"). Each textual fact is then provided from the fact extractor computing device 102 to the fact linker computing device 106.

The fact extractor computing device 102 is and/or includes, but is not limited to, a desktop, laptop, tablet, mobile device (e.g., smartphone device, or other mobile device), server, computing system and/or other types of computing entities that generally comprises one or more communication components, one or more processing components, and one or more memory components.

The fact linker computing device 106 is a computing device that is configured to set up a reference KG that includes a set of entities, a set of relations, and/or a set of facts. Additionally, and/or alternatively, the fact linker computing device 106 creates an enriched KG via for each triple and each element in the triple, ranking against entities/relations in the reference KG and/or deciding (e.g., determining) if the element should be linked to an existing KG entity/relation or if it should become a new entity/relation. Additionally, and/or alternatively, the fact linker computing device 106 can further provide the enriched KG to a KG predictor to determine (e.g., derive the final outcome).

The fact linker computing device 106 is and/or includes, but is not limited to, a desktop, laptop, tablet, mobile device (e.g., smartphone device, or other mobile device), server, computing system and/or other types of computing entities that generally comprises one or more communication components, one or more processing components, and one or more memory components.

The database 108 includes one or more knowledge graphs (KG) 110. A knowledge graph (e.g., a semantic network) represents a network of entities (e.g., objects, events, situations, and/or concepts), and illustrates the relationships (e.g., relation) between each of the entities. For instance, in a triple, the entities can include the subject (e.g., the starting point) and the object (e.g., the ending point). The relation describes the relationship that links the subject to the object. In some instances, the KG 110 can include nodes and/or edges. The nodes can represent the entities (e.g., subject and object) and the edges can represent the relation between the nodes/entities. In some variations, a single node from the KG 110 can include one or more relations to one or more other nodes. For instance, a subject can be linked to multiple objects, and the relation between the subject to the multiple objects can be different.

The database 108 is and/or includes, but is not limited to, a storage entity that stores data such as KGs 110 (e.g. reference and/or enriched KGs). In some instances, the database 108 may be a repository (e.g., a data repository). In other instances, the database 108 may include a computing device such as a desktop, laptop, tablet, mobile device (e.g., smartphone device, or other mobile device), server, computing system and/or other types of computing entities that generally comprises one or more communication components, one or more processing components, and one or more memory components.

It will be appreciated that the exemplary system depicted in FIG. 1 is merely an example, and that the principles discussed herein may also be applicable to other situations—for example, including other types of devices, systems, and network configurations. For instance, in some embodiments, a single computing platform (e.g., a server) can perform the functionalities of the fact extractor computing device 102 and the fact linker computing device 106 and/or include a database that stores the knowledge graphs 110. In such embodiments, the single computing platform might not use the network 104 to perform the functionalities of the fact extractor computing device 102 and the fact linker computing device 106.

Figure 2:
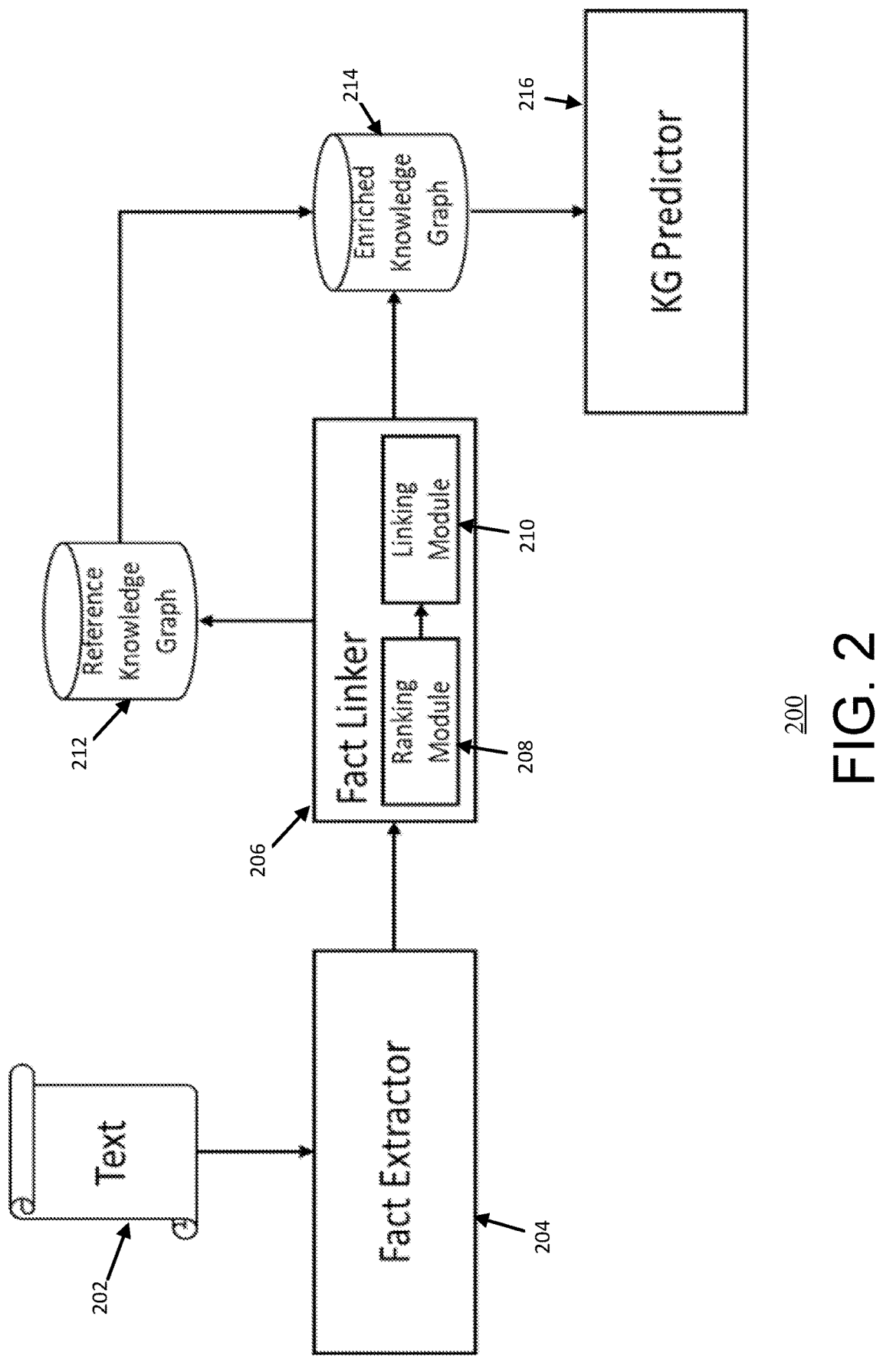
FIG. 2 illustrates another simplified block diagram depicting an exemplary system according to an embodiment of the present disclosure.

Embodiments of the present invention operate as part of a larger system, which is depicted in FIG. 2. FIG. 2 illustrates a simplified block diagram depicting an exemplary system according to an embodiment of the present disclosure. For instance, the system 200 includes text 202, fact extractor 204, fact linker 206, reference knowledge graph 212, enriched knowledge graph 214, and knowledge graph (KG) predictor 216. The fact linker 206 includes ranking module 208 and linking module 210. The ranking module 208 and the linking module 210 is and/or includes engines, processors, and/or memory storing executable instructions. For instance, the ranking module 208 and the linking module 210 can store executable instructions that when executed by one or more processors are configured to perform one or more functions described below. Additionally, and/or alternatively, the ranking module 208 and/or the linking module 210 includes hardware components (e.g., controllers and/or processors).

In some instances, the fact extractor 204 is the fact extractor computing device 102 of FIG. 1 and the fact linker 206 is the fact linker computing device 106 of FIG. 1. Additionally, and/or alternatively, the fact linker computing device 106 performs the KG predictor 216. In other instances, as mentioned above, a single computing platform performs the functionalities of both the fact extractor 204 and the fact linker 206. Additionally, and/or alternatively, the single computing platform and/or a separate computing device performs the KG predictor 216.

Referring to system 200, given text of interest, embodiments of the present invention first use a fact extractor 204 to turn the text 202 into a set of facts, where each fact takes the form of a triple: ("subject", "relation", "object"). For instance, the fact extractor 204 converts the text 202 into a set of facts in the form of the triple, "subject", "relation", "object". Each textual fact is then passed on to (e.g., provided to) the fact linker 206. The fact linker 206 has access to a reference knowledge graph 212. This reference knowledge graph 212 keeps track of a set of entities, a set of relations, and/or a set of facts, such as (e1, r, e2), where e1 and e2 are part of the set of entities and r is part of the set of relations. For instance, the fact linker computing device 106 can access the reference knowledge graphs 212, which can be stored in the databases 108.

As used herein for clarity, facts from text are referred to as textual facts and facts from the KG are referred to as KG facts. Additionally, and/or alternative, the system 200 keeps track of which textual facts/entities/relations have been linked to which KG facts/entities/relations. For this, the system 200, for example, can keep a dictionary for both textual and KG entities and relations. For instance, this can be performed such as an "KG entity to textual entity" mapping: e.g., {e1: t1, t2, t3; e2: t4, t2}; a "Textual entity to KG entity mapping": {t1: e1; t2: e1, e2; t3: e1; t4: e2}; analogously for relations and facts.

The fact linker 206 then iterates over each textual fact and each entry (e.g., slot) in a fact. For each entry ("subject", "relation", "object"), the fact linker 206 determines whether the slots of the textual fact should be linked to an existing entity or relation in the reference KG 212 or not. If the textual fact should be linked, then the entity or relation from the text is assigned an entity or relation from the reference KG 212. If it should not be linked, then a new entity or relation is added to the reference KG 212. The final output of this step is an enriched knowledge graph 214. This enriched knowledge graph 214 can in turn be given (e.g., provided) to a KG predictor 216, which can for example predict missing links or classify nodes, depending on corresponding embodiment. This will be described in further detail below.

Embodiments of the present invention utilize a fact linker 206. The fact linker gets (e.g., obtains) as input a set of textual facts in the form of triples from the fact extractor 204. For example, the fact linker 206 can obtain the following facts as input: ("CD8 T cells", "play a crucial role in", "cancer immunity"), ("antimalarial"; "is used to treat", "malaria"), etc. For each fact, the fact linker 206 inspects each of the slots; e.g., the subject, relation and the object. Then, the fact linker 206 checks whether the slot can be linked to the reference knowledge graph 212. If the slot can be linked to the reference knowledge graph 212, the fact linker 206 proceeds with the linking step, where the fact linker outputs a reference ID for the entity or relation. If the slot cannot be linked to the reference knowledge graph 212, then the fact linker 206 outputs a special symbol, which indicates that the entity or relation is not found in the KG (e.g., "nil"). Subsequently, a new entity or relation with a unique identifier is added to the KG and the textual representation is saved. Therefore, a new enriched knowledge graph 214 is generated by the fact linker 206. This will be described in further detail below. In some embodiments, the fact linker 206 has access to the reference knowledge graph 212 in order to perform these steps. In some variations, the fact linker includes two parts: (1) the coverage module (e.g., ranking module 208): determines whether the target slot is covered by the reference KG 212; (2) disambiguation module (e.g., the linking module 210): links the slot from the open information extraction (OpenIE) fact to the reference KG entity/relation.

The ranking module 208 is described below. For instance, the problem of linking textual facts to a Knowledge Graph (e.g., the reference KG 212) can be posed as a retrieval problem. The number of entities in modern Knowledge Graphs is large; e.g., the publicly available WIKIDATA Knowledge Graph contains circa 55 million (M) entities. Therefore, training standard discriminative (classification) models is prohibitive. For instance, for each entity slot of the textual fact (e.g., subject or object), the inner product is computed between the text entity embedding and the embedding of each Knowledge Graph entity. The inner product can be computed in order to determine the similarity between the KG entity and the textual entity. Since this is a ranking model, the KG entity with the highest similarity is considered as the corresponding entity for the textual fact. In some instances, the text entity embeddings are vector representations of the subject/object textual phrases. Embodiments of the present invention can be flexible in how these embeddings can be derived: e.g., they can be computed by adding up the word embeddings containing the phrase, which can be derived from any embedding layer that was learned elsewhere (e.g., pre-trained language models such as BERT (see e.g., Jacob Devlin, Ming-Wei Chang, Kenton Lee, Kristina Toutanova: "BERT: Pre-training of Deep Bidirectional Transformers for Language Understanding", arXiv: 1810.04805, 2018, the entire contents of which, are hereby incorporated by reference herein) or GPT (see, e.g., Alec Radford, Karthik Narasimhan: "Improving Language Understanding by Generative Pre-Training", Corpus ID: 49313245, 2018, the entire contents of which, are hereby incorporated by reference herein), word2vec (see, e.g., Tomas Mikolov, Kai Chen, Greg Corrado, Jeffrey Dean: "Efficient Estimation of Word Representations in Vector Space", arXiv: 1301.3781, 2013, the entire contents of which, are hereby incorporated by reference herein) or GloVe (see, e.g., Jeffrey Pennington, Richard Socher, and Christopher Manning: "GloVe: Global Vectors for Word Representation", In Proceedings of the 2014 Conference on Empirical Methods in Natural Language Processing (EMNLP), pages 1532-1543, Doha, Qatar. Association for Computational Linguistics, 2014, the entire contents of which, are hereby incorporated by reference herein) approaches). In other words, in some variations, the ranking module 208 may determine the text entity embeddings as vector representations of the subject/object textual phrases using one or more methodologies, algorithms, models (e.g., machine learning models), and/or other processes.

Embodiments of the present invention build the textual fact linking model as a two-tower model, which is demonstrated to perform well across different tasks, e.g., Contrastive Image-Text Retrieval (see, e.g., Alec Radford, Jong Wook Kim, Chris Hallacy, Aditya Ramesh, Gabriel Goh, Sandhini Agarwal, Girish Sastry, Amanda Askell, Pamela Mishkin, Jack Clark, Gretchen Krueger, Ilya Sutskever: "Learning Transferable Visual Models From Natural Language Supervision", arXiv: 2103.00020, 2021, the entire contents of which, are hereby incorporated by reference herein). Embodiments of the present invention include a model formulation that is novel over the current state of the art (see e.g., Zhengbao Jiang, Jialong Han, Bunyamin Sisman, Xin Luna Dong: "CoRI: Collective Relation Integration with Data Augmentation for Open Information Extraction", ACL/IJCNLP (1) 2021:4706-4716; Dongxu Zhang, Subhabrata Mukherjee, Colin Lockard, Xin Luna Dong, Andrew McCallum: "OpenKI: Integrating Open Information Extraction and Knowledge Bases with Relation Inference", NAACL-HLT (1) 2019:762-772; and Ian D. Wood, Mark Johnson, Stephen Wan: "Integrating Lexical Information into Entity Neighbourhood Representations for Relation Prediction", NAACL-HLT 2021:3429-3436, the entire contents of which, are hereby incorporated by reference herein). For instance, embodiments of the present invention perform linking of all textual fact slots (subject, object and relation) jointly to the entire reference knowledge graph 212. For example, traditionally, problems of linking textual facts to Knowledge Graphs can be related to both entity linking and relation inference problems. Current entity linking methods, however, are unable to link relation to knowledge graphs, and it is unclear how traditional methods deal with scenarios such as whether the link is polysemous (e.g., entity span that might refer to multiple KG entities). Compared to prior art entity linkers (e.g., BLINK, GENRE), embodiments of the present invention can link both entities and relations to a large scale KG, and implement a tailor-made module for dealing with polysemous entities (e.g., aggregation of the graph-based entity embeddings). On the other end, certain approaches (e.g., OpenKI, CORI) perform linking of the textual fact's relation to a Knowledge Graph relation. These methods make the assumption that the entities are linked apriori, which is generally not the case in practice.

In some embodiments, the model (e.g., the textual fact linking model used by the fact linker 206) consists of and/or includes a textual fact embedding model, and a Knowledge Graph embedding model. The textual fact embedding model can be for example a pretrained language model (e.g., a pretrained natural language processing (NLP) model), such as RoBERTa (see, e.g., Yinhan Liu, Myle Ott, Naman Goyal, Jingfei Du, Mandar Joshi, Danqi Chen, Omer Levy, Mike Lewis, Luke Zettlemoyer, Veselin Stoyanov: "RoBERTa: A Robustly Optimized BERT Pretraining Approach", arXiv: 1907.11692, 2019, the entire contents of which, are hereby incorporated by reference herein), which can be subsequently fine-tuned on a dataset that is collected.

The input layer of the pretrained language model is modified in a novel fashion over the current state of the art, e.g., three special randomly initialized tokens are added and/or used to obtain an embedding for each textual fact slot separately. For example, the textual fact ("antimalarial"; "is used to treat", "malaria") is represented as "<SUBJ> antimalarial <REL> is used to treat <OBJ> malaria". The fact representation is tokenized and provided to the pre-trained language model and embeddings are obtained for each textual fact slot, for example, by selecting the hidden representation of the special tokens or by performing a pooling operation across the relevant subtokens. For instance, embeddings for each slot is obtained. For example, "antimalarial" is one embedding vector, "is used to treat" is another, and "malaria" is a third embedding vector. The final fact representation is determined by tokenizing the concatenated string "<SUBJ> antimalarial <REL> is used to treat <OBJ> malaria" and obtaining a vector representation of the entire fact by, for example, performing a pooling operation across the relevant subtokens. In some embodiments, the fact linker 206 (e.g., the ranking module 208) obtains textual facts (e.g., a subject, a relation, and an object such as "antimalarial" as the subject, "is used to treat" as the relation, and "malaria" as the object). The fact linker 206 uses a pretrained language model (e.g., a pretrained NLP model such as RoBERTa) for the textual fact. For instance, the fact linker 206 modifies the input layer of the pretrained language model by including three special randomly initialized tokens for each of the slots of the textual fact (e.g., a first token for the subject, a second token for the relation, and a third token for the object). The fact linker 206 provides the tokenized textual fact to the pretrained language model, and embeddings (e.g., a vector of values) are obtained for each textual fact slot (e.g., three vectors are obtained for the object, relation, and subject).

The knowledge graph embeddings (e.g., entities and relations) are obtained using two models in conjunction. To obtain text entity embeddings, the same embedding model (e.g., RoBERTa) that was used for the textual fact is reused for this part. To prepare the KG entity input in a similar form as the textual fact input, the entity name is used, concatenated with a special <ENT> token, followed by any additional entity information available from the Knowledge Graph, e.g., a textual description. In some examples, if no descriptions found in the KG, the first occurrence of a textual fact as a description can be used. For example, in some embodiments, if there is a textual fact that includes an entity that is new to the KG (e.g., it does not exist in the KG), then this entity is then added to the KG as a new entity. Therefore, it does not have a textual description (also, this might happen even to already existing entities). When this happens, embodiments of the present invention take the first textual fact where this entity appeared (e.g., which was extracted by the fact extractor) and embodiments of the present invention concatenate the textual fact "subject+ relation+object" as a description, which is then added to the KG.

For example, the entity "antimalarial" can be encoded as "antimalarial <ENT> agents used in the treatment of malaria". Finally, the entity embedding from the Language Model is obtained. For instance, in some variations, the fact linker 206 uses two models in conjunction for the KGs (e.g., the reference knowledge graphs 212) to obtain the knowledge graph embeddings for the entities and relations. The first model that is used (e.g., RoBERTa) can be the same model that is used for the textual fact. Similar to the textual fact, the fact linker 206 uses special tokens for the entities. For instance, for the entity "antimalarial", the fact linker 206 includes a special token ("<ENT>") after the entity "antimalarial", and also includes a textual description and/or a first occurrence of the textual fact (e.g., "agents used in the treatment of malaria"). As such, for the entity "antimalarial", the fact linker 206 may determine a text string "antimalarial <ENT> agents used in the treatment of malaria" for the entity, which is provided to the first model (e.g., the language model such as RoBERTa) to obtain a first embedding for the knowledge graph.

If a polysemous entity mention is given without context, the text entity embedding might not be sufficient to disambiguate the correct link. For example, "CTL" can refer to both a cell (the Cytotoxic T Cell) and the engineering process (coal-to-liquid). To alleviate this issue, the graph-based entity and relation embedding model (e.g., frozen KG embeddings) are used. For instance, to obtain the knowledge graph embeddings, the fact linker 206 uses a second model (e.g., the graph-based entity and relation embedding model/ frozen KG embeddings) to disambiguate for polysemous entities. The fact linker 206 can learn the graph-based embeddings for both the entities and the relations using the knowledge graph embedding model.

In some instances, to prepare the KG entity input in a similar form as the textual fact input, embodiments of the present invention use the entity name, concatenated with a special <ENT> token, followed by any additional entity information available from the Knowledge Graph (e.g., a textual description). Therefore, the entity "antimalarial" can be encoded as "antimalarial <ENT> agents used in the treatment of malaria". Further, embodiments of the present invention obtain the entity embedding from the Language Model. For the second model, embodiments of the present invention use KG graph-based embeddings from entities and relations. The output can be a link for each slot to a KG entry (e.g., for subject, relation or object). If one has "CTL" as input, depending on the context, the fact linker can either output a reference ID for the Cytotoxic T Cell or a reference for the engineering process (coal-to-liquid).

Embodiments of the present invention provide a method that is agnostic with respect to (w.r.t.) the model (e.g., the graph-based entity and relation embedding model) itself (e.g., one could use TransE (see, e.g., Antoine Bordes, Nicolas Usunier, Alberto Garcia-Durán, Jason Weston, Oksana Yakhnenko: "Translating embeddings for modeling multi-relational data", NIPS '13: Proceedings of the 26th International Conference on Neural Information Processing Systems-Volume 2, 2013, the entire contents of which, are hereby incorporated by reference herein)). These embedding (e.g., by using a knowledge graph embedding model, such as TransE) are trained. In some embodiments, the embeddings (e.g., the frozen KG embeddings) can, for example, be stored offline on a disk; e.g., these embeddings are not fine-tuned further as the process is prohibitive given the size of the Knowledge Graph. Additionally, and/or alternatively, the embeddings can be updated at some defined interval. For instance, the fact linker 206 can store the embeddings offline on a disk and/or can update the embeddings at some defined interval.

If the number of entities is large, training a standard classification model is prohibitive. Therefore and in order to improve performance, the model (e.g., the overall model shown in FIG. 3) is trained using a contrastive loss (e.g., the InfoNCE loss (see, e.g., Aäron van den Oord, Yazhe Li, "Oriol Vinyals: Representation Learning with Contrastive Predictive Coding", CoRR abs/1807.03748, 2018, the entire contents of which, are hereby incorporated by reference herein)). The contrastive loss in one-way is applied, e.g., for each textual fact embedding, negative Knowledge Graph embeddings obtained and the loss is measured, but not the other way around. For instance, the fact linker 206 can train the model using contrastive loss and apply it in one-way. During training, the model learns to output embeddings of textual facts in the same (shared) latent space as the Knowledge Graph embeddings. In other words, in some embodiments, after training, the embeddings of the textual entities and relations should be close to their canonical Knowledge Graph counterpart in the shared latent space.

The textual fact linking inference is structured as a retrieval problem, and the fact linker 206 creates the retrieval indices for the entities and the relations separately. For the entity linking, the entities are clustered first and then added to the clusters. When linking the textual entities (subject and object), the most similar cluster is selected, for example by performing approximate nearest neighbor search with n probes and selecting the most similar n centroids (e.g. based on cosine similarity). Then, search is performed within each cluster for the predicted entity links. As the number of relations is significantly smaller, the retrieval index is deterministic, and the most similar relation link is retrieved as the prediction. While the number of relations is usually significantly smaller in real scenarios, embodiments of the present invention is applicable for cases that have any size of entities and relations (e.g., where the number of relations is also large, or in cases where the number of entities and relations is relatively small).

In some embodiments, optionally, to achieve faster inference, the embeddings can be compressed, for example by applying Principal Component Analysis on the Knowledge Graph embeddings to decrease their dimensionality (e.g., from 200 to 64), followed by a K-Means clustering with k number of centroids, where k is typically large number (e.g., 218). During inference, the model outputs embeddings of textual entities (subject and object) and embeddings of relations.

Figure 3:
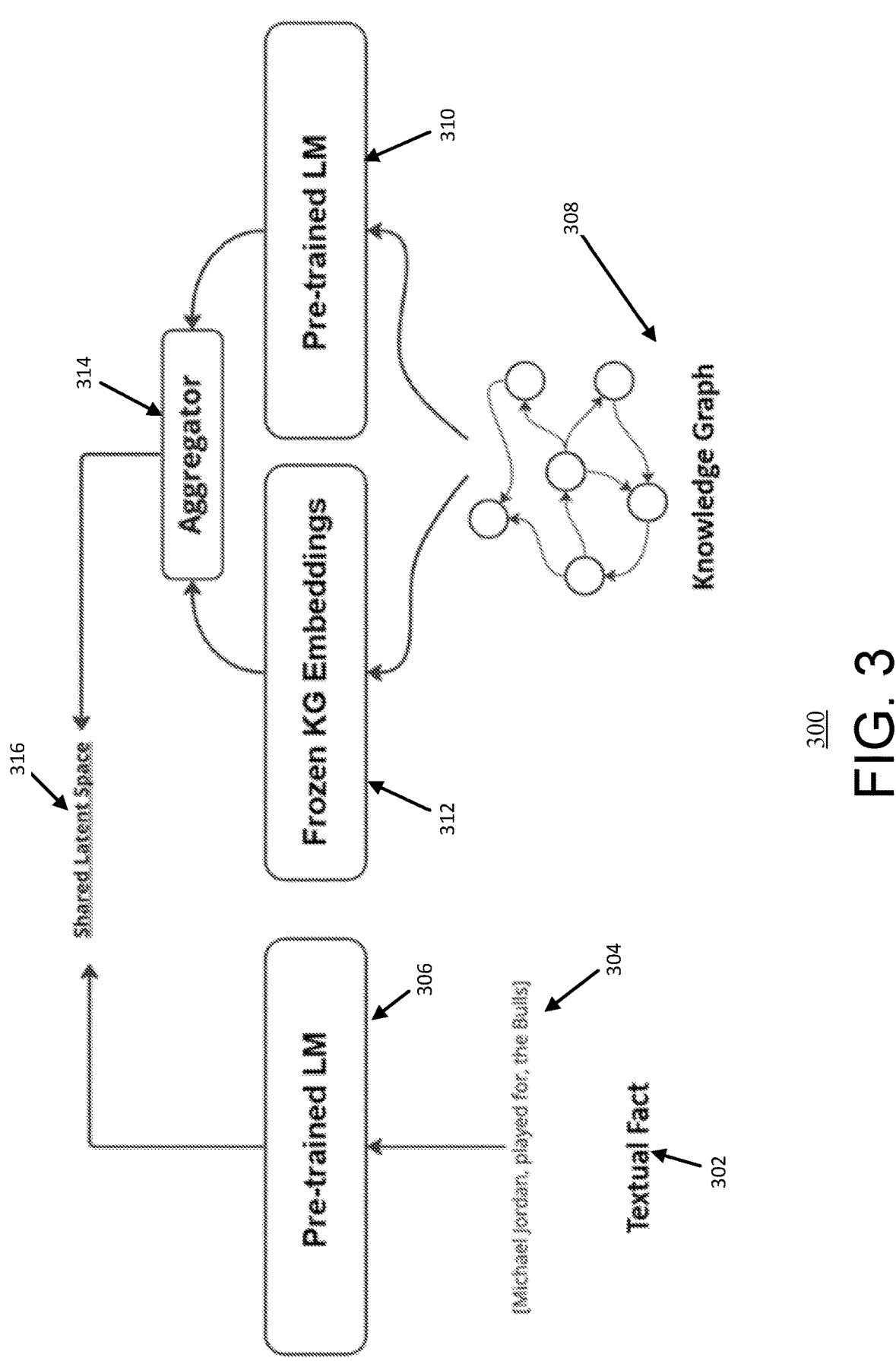
FIG. 3 illustrates an exemplary overall architecture of a disambiguation module from a fact linker according to an embodiment of the present disclosure.

FIG. 3 illustrates an exemplary overall architecture of a disambiguation module (e.g., ranking module 208) from a fact linker 206 according to an embodiment of the present disclosure. For instance, the ranking module 208 can perform the architecture 300. The architecture 300 includes the textual fact 302, which for example, is the fact 304 (e.g., "[Michael Jordan, played for, the Bulls]"). The subject is Michael Jordan, the relation is played for, and the object is the Bulls.

The architecture 300 further includes the pre-trained language model (LM) 306 such as an NLP model (e.g., RoBERTa). For instance, the fact linker 206 includes tokens (e.g., "<ENT>") for each of triple (e.g., subject, relation, object) and provides the result to the pre-trained LM 306. As mentioned above, the input layer of the pre-trained LM 306 is modified to accept the textual fact 302 with the modification of the tokens and/or sub-tokens. The fact linker 206 obtains textual fact embeddings based on providing the modified textual fact into the pre-trained LM 306. For instance, the textual fact embeddings indicates a textual fact embedding for each of the slots of the textual fact 302 (e.g., a textual fact embedding for the subject, "Michael Jordan", a textual fact embedding for the relation, "played for", and a textual fact embedding for the object, "the Bulls"). The textual fact embedding can be a vector.

The fact linker 206 uses the frozen KG embeddings and the pre-trained LM 310 (e.g., the two models) to determine knowledge graph embeddings for the knowledge graph 308. For instance, the knowledge graph 308 can be the reference knowledge graph 212. The pre-trained LM 310 is similar to the pre-trained LM 306. For instance, the fact linker 206 can use the same pre-trained LM 306 (e.g., RoBERTa) for the pre-trained LM 310. In operation, the fact linker 206 modifies the entities and relations from the knowledge graph 308 such as by including tokens mentioned above. Further, the fact linker 206 can include a textual description and/or a first occurrence of the textual fact for the entity and/or relations. The fact linker 206 inputs the modified entities and relations from the knowledge graph 308 into the pre-trained LM 310 to obtain intermediate knowledge graph embeddings (e.g., intermediate knowledge graph embeddings for the object, relation, and/or subject).

Using the graph-based entity and relation embedding model, the fact linker 206 determines the frozen KG embeddings 312. For instance, the input to 312 can be the KG entity/relation from the knowledge graph 308 and the output of 312 that is provided to the aggregator 314 can be the KG entity/relation embedding vector.

The fact linker 206 then uses the aggregator 314 based on the outputs from the two models (e.g., the pre-trained LM 310 and the frozen KG embeddings 312). For instance, the aggregator 314 can be, for example, concatenating the embedding vectors from the frozen KG embeddings 312 and the pre-trained LM 310.

Afterwards, using the knowledge graph embeddings from the aggregator 314 and the textual fact embeddings from the pre-trained LM 306, the fact linker 206 determines an output for the ranking module 208. The output is in a shared latent space 316. For instance, the fact linker 206 creates retrieval indices for the entities and the relations separately. For instance, the fact linker 206 can use one or more clustering algorithms (e.g., k-means clustering) to determine clusters.

Figure 4:
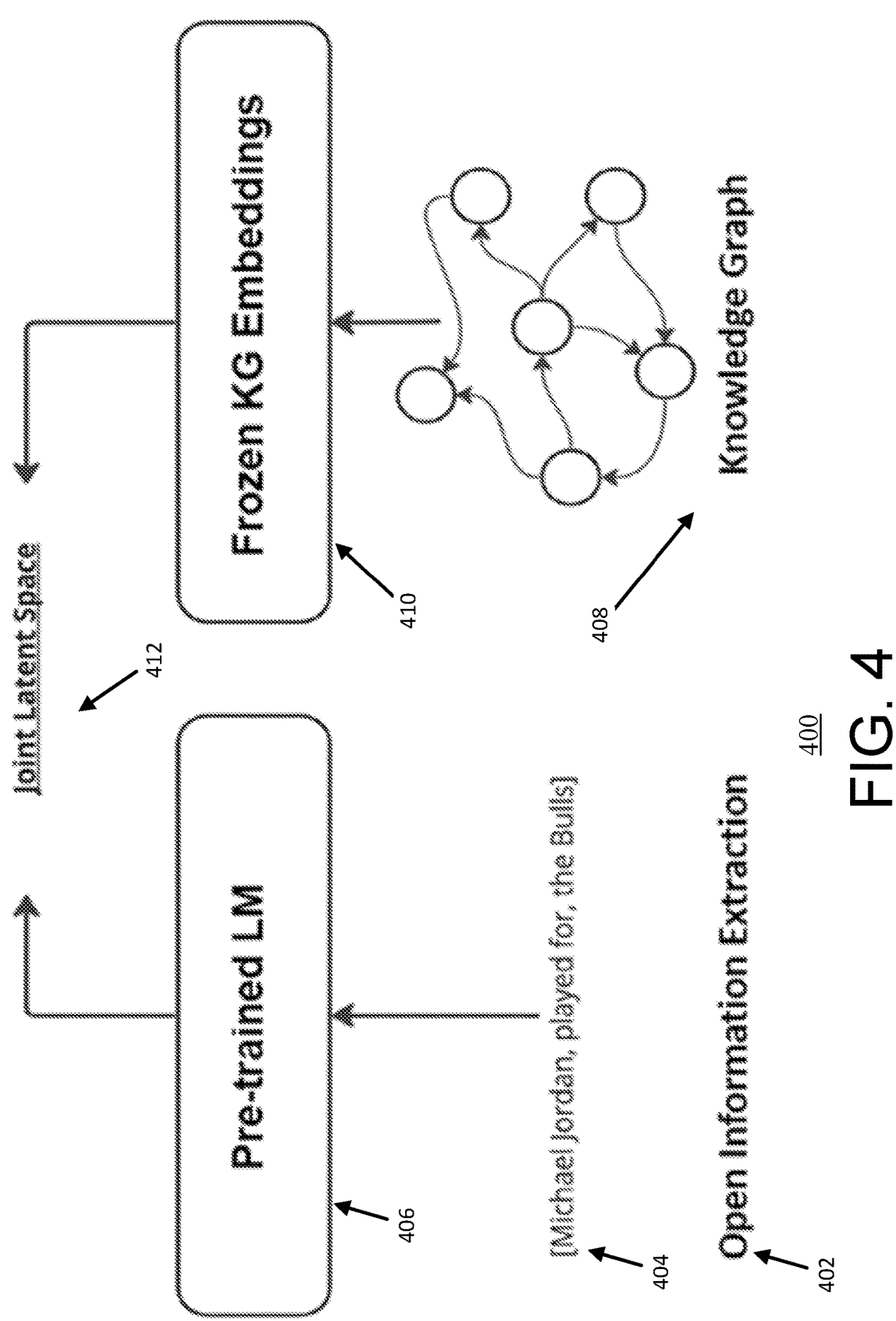
FIG. 4 illustrates a disambiguation module from a fact linker according to an embodiment of the present disclosure.

FIG. 4 illustrates a disambiguation module from a fact linker according to an embodiment of the present disclosure. For instance, FIG. 4 shows a disambiguation module 400 for training frozen KG embeddings. For example, the disambiguation module 400 includes open information extraction 402, the fact 404 (e.g., "[Michael Jordan, played for, the Bulls]"), the pre-trained LM 406, the knowledge graph 408, the frozen KG embeddings 410, and the joint latent space 412.

The linking module 210 will be described below. For example, for each textual subject/relation/object, the output from the ranking module 208 is an ordered list over the entities/relations from the reference KG 212, where textual subjects and objects have corresponding KG entities and textual relations have corresponding KG relations. For instance, for each fact, the output from the ranking module 208 indicates the textual subjects and objects from the textual fact 302 as well as the corresponding linking from the KG entities (e.g., the KG subjects and objects) from the knowledge graph 308. Similarly, the output indicates the textual relation from the textual fact 302 and the corresponding linking for the KG relation from the knowledge graph 308.

For example, without loss of generality, let the candidate c be the subject, the relation or the object. Iterating over each in turn, the respective KG ranking is then iterated over. Each KG entry n is considered in turn and starts with the entry with the highest ranking (e.g., the KG link or most likely the KG link) and goes down the list until the linking step confirms that candidate c should be linked to KG entry n. For each candidate c and KG entry n pair, a corresponding feature vector is built and a method is created that takes this as input and outputs the decision whether candidate c and entry n should be linked. For instance, the fact linker 206 (e.g., the linking module 210) generates (e.g., builds) a feature vector. The fact linker 206 uses the feature vector as an input and outputs a decision whether candidate c and entry n should be linked. For example, the fact linker 206 can use the inner product computed between the text entity embedding and the embedding of each Knowledge Graph entity to determine (e.g., confirm) that the candidate c is to be linked to the KG entry. For instance, as mentioned previously, the inner product is used for linking. The fact linker 206 builds the feature vector with features (e.g., ranking score, previous link, and other components described below). Each entry in the vector can be defined, and the value of each entry in the vector is determined automatically. This will be described below.

The feature vector can include the below components.

Ranking score: a scalar, obtained as output from the Ranking module, which indicates how likely the candidate c and the entry n should be linked. For example, this can be (1) an unnormalized score, (2) a probability score, (3) the ranking itself.

Previous link: The KG mapping is used to retrieve possible previous KG entries that the candidate c has been linked to. The KG mapping can indicate whether the current candidate text (e.g., "CTL") is linked previously to something else (e.g., to another entity in the KG, which is different from the current entry n). If the candidate c has not been previously linked, the value is set to None, and otherwise, the entity/relation embedding of the previous link is included. For example, Text entity/candidate c: "CTL", current entry n: "CTL the cytotoxic T cell". Previously "CTL" has also been linked to another entry: "CTL the coal-to-liquid engineering process". Therefore, the other link is set to 1.

Current link: the current KG mapping of the Ranking module is used. That is, the embedding of the entity/relation that the candidate c can be potentially linked to is used.

Current link additional information: From the KG, any additional information for the proposed entry n is obtained. This could be the description of the entity, its aliases, etc.

Closest text: the KG mapping is used to retrieve possible text entities for the current KG entry n. For each existing text entity, this mention is encoded in the same way as the candidate c. Based on this, which other existing text entity is most similar to is computed and this value is recorded for the variable closest text. For example: Candidate c: "CTL", entry n "CTL the cytotoxic T cell". Previously the text "cytotoxic T cell" and "T-killer cell" was linked to entry n. "cytotoxic T cell" has higher similarity to "CTL" than "T-killer cell". How similar "CTL" and "cytotoxic T cell" are to each other is kept.

In some embodiments, other components are added or can be added if desired.

All features can then be aggregated. Such aggregation of features can be done, for example, by concatenating all of them (e.g., the ranking score can be concatenated with the previous link, current link, current link additional information, closest text, and so on), while additional performance improvement can be obtained with more sophisticated feature aggregation methods such as Transformers, Bi-directional RNNs, etc. For instance, the fact linker 206 aggregates the features of the generated feature vector. For example, the fact linker 206 can aggregate the features of the generated feature vector by concatenating each of the features (e.g., the strings) together. Additionally, and/or alternatively, the fact linker 206 can perform one or more additional feature aggregation methods such as Transformers and/or Bi-directional RNNs.

Given the aggregated feature vector, embodiments of the present invention proceeds with the decision-making module that is a binary classifier, which for example, outputs a probability score how likely it is that the candidate should be linked and to convert the probability score into a decision, and thresholding is performed. For instance, the linking module 210 can perform the binary classifier. The linking module 210 takes into account the final score from the binary classifier (e.g., which outputs some score in the interval of [0,1]). Then, based on a threshold, the linking module 210 (e.g., binary classifier) brings a decision whether or not the entity/relation is to be linked (e.g., this decision is either 0 or 1). This is performed by thresholding (e.g., if score >0.5, then decision is 1). The probability score can determined, for example, by simple softmax layer in the neural network, which can give probability-like scores. In other words, based on the aggregated feature vector, the linking module 210 can perform the binary classifier (e.g., using one or more operations or methods such as a softmax layer in the neural network), which outputs one or more scores on an interval such as between 0 and 1. The linking module 210 can take into account a final score determined from the binary classifier and compare it with a threshold. Based on the comparison (e.g., if the score is greater than 0.5), the linking module 210 can determine a decision as to whether or not the entity/relation is to be linked. The decision can be binary (e.g., 0 or 1) indicating whether the entity/relation is to be lined.

Based on the binary decision, it is then determined whether the linking of candidate c and KG entry n should or can take place. For instance, if the entities and/or relations from the textual fact are to be linked to the reference KG, embodiments of the present invention check if such fact actually exists already. If it doesn't, then embodiments of the present invention add it to the KG. If, however, at least one of the textual slots (e.g., subject, relation or object) is not linked to the KG, then by definition this fact is not present in the KG. In such scenario, embodiments of the present invention adds the new entity/relation to the KG, as well as the extracted fact with it. From this, it follows that if the KG is initially empty, then every first textual fact can be with new entities and relations. These, then, are added directly to the KG, along with the accompanying facts. For example, based on the binary decision, the system 200 (e.g., the fact linker 206 and/or the linking module 210) determines whether the entities and/or relations from the textual fact (e.g., the candidate c) should or could be linked to the KG entry n. If so, the system 200 determines whether the fact already exists in the KG, and if it doesn't the system 200 adds it to the KG. For instance, if at least one of the textual slots is not linked to the KG (e.g., if the object is not within the KG), then the system 200 determines that this fact is not present in the KG and adds the new entity/relation to the KG as well as the extracted fact with it. Initially, in some embodiments, the KG can be empty, and the system 200 can add facts including new entities and relations to the KG.

The technical fields and/or uses of the embodiments of the present invention are described below.

For instance, in some embodiments, embodiments of the present invention are used for robust drug development with resistance to machine-induced errors. For instance, this can be applied to provide improvements to the technical field of automated AI drug development. The use case can include optimizing and calibrating of extracted chemical compounds from libraries of textbooks and publications. The linking module helps in building high-quality canonical knowledge graph from pure text resources. The data sources can include Libraries of textbooks and publications. Embodiments of the present invention can link the extracted textual facts to already established entities and/or relations. In addition, embodiments of the present invention can generate new concepts in the KG if they do not exist already. The output can include discovering new (canonical) facts from text data that contain information about using a particular drug to treat a particular patient. The output can further include adding this fact to the knowledge graph or building new one from scratch. For physical change (technicity): the output of the linked facts can contain information about using a particular drug to treat a particular patient, as well as how to treat the patient. Because embodiments of the present invention can discover new (open) facts that may contain entities or relations that do not exist in the reference knowledge graph, the open nature of the facts allows for a wide variety of recommendations; e.g., suggesting a specific chemical for directly treating the patients.

For example, the textual fact can be ("CD8 T cells"; "play a crucial role in"; "cancer immunity"). The links to WIKI-DATA as a reference knowledge graph is provided. For instance, "CD8 T cells"→ID: Q188930, Text description: "cytotoxic T cell", details. "play a crucial role in"→ID: P1537, Text description: "contributing factor of", details. "cancer immunity"→not in knowledge graph.

In some embodiments, embodiments of the present invention are used for material informatics. For instance, this can be applied to provide improvements to the technical field of automated materials development. The use case can include linking extracted textual facts (about the properties of mate-rials from text and log files) to a domain-specific reference knowledge graph. This would reduce the time and the costs of errors in the wet-lab costs of material design. The data source can include research papers, scientific reports, and log files describing the behavior of materials, tester feed-back, such as the melting point. Embodiments of the present invention can link the extracted textual facts to a reference knowledge graph. In addition, if parts of the textual facts cannot be linked, embodiments of the present invention generates new concepts for the reference knowledge graph (e.g., new entity/entities and/or new relation(s)). The list of linked facts can be output. For physical change (technicity): embodiments of the present invention fixes the synthesis process of rubber materials by suggesting corrections on the procedure based on the linked textual facts. For example, one newly linked fact would discover automatically that rubber X fails for a reason Y, while another corrected extraction suggests a particular method to fix it.

In some embodiments, embodiments of the present invention are used for inventory items. For instance, this can be applied to provide improvements to the technical field of smart plants for inventory management. The use case can include extracting and linking the extracted information about the stored items in a facility (e.g., warehouse). The data source can include facility reports, logs, etc. Embodiments of the present invention can link (to a reference knowledge graph) extracted textual facts describing the items and where they are located in the facility. In addition, embodiments of the present invention can include a method that generates new entities and/or relations to the reference knowledge graph in case they are not present. Further, embodiments of the present invention is capable of generating the knowledge graph from scratch from textual resources. The output can include a list of linked facts. For physical change (technicity), linking of the extracted facts to a reference knowledge graph can be performed. Based on the information contained within these linked facts, which contain information about items and robots in the inventory and their location, another AI system can be executed that sends robots in the facility to move the items in the right location.

In some embodiments, embodiments of the present invention are used for detection and correction of suspects from textual messages. For instance, this can be applied to provide improvements to the technical fields of smart cities or automated law enforcement. The use case can include linking textual facts to reference knowledge graph is important in sensitive domains. The linking helps in disambiguating the entities in the textual facts, which in turn helps in optimizing legal procedures. The data source can include email text messages, police reports, court protocols, and witness questioning. Embodiments of the present invention can extract textual facts from natural language text and links them to reference knowledge graph. A list of linked textual facts can be output. For physical change (technicity), the filing of legal actions and police investigations against suspects that were wrongly missed by ambiguous textual facts can be performed. These facts contain information about potential suspects, what kind of crime they are sus-pected of, etc. Based on the resolved ambiguities by the fact linker, embodiments of the present invention are used to detect if someone is a suspect. This event triggers the situation where the data is written on separate part of the disc due to security reasons.

Embodiments of the present invention provide for the following improvements over existing technology:

1. Utilizing and modifying a pre-trained language model to encode a textual fact of the form (subject, relation, object) and marking each element in the text by inserting specific markers for subject, relation and object, respectively.

2. A model trained in a contrastive setting, projecting textual fact embeddings (all slots-subject and object entities and relations) in a joint latent space as knowledge graph fact embeddings, obtained from both large language models and knowledge graph embedding models, both contributing towards a system which can link monosemous and polysemous entity mentions.

3. A module (e.g., hardware components and/or software components, capable of recognizing whether each of textual fact slots are present in the knowledge graph. The module creates a custom feature vector based on the output of the Ranking module and outputs a binary decision indicating the presence of each slot (subject, relation, and object). An overview of the different features is described above.

4. The fact linker, which is configured to provide the linking step, where the fact linker outputs a reference identifier (ID) for the entity or relation.

The technical advantages can further include additional information that can be obtained from the KG (e.g., the entity description, its aliases, etc.).

In an embodiment, the present invention provides a method for disambiguating facts by linking them to a reference KG and introducing the concepts (entities and relations) if needed or desired. The method comprises the steps of:

1. Getting (e.g., obtaining) the textual data of interest.

2. Running a fact extractor on 1) that turns text into a set of triples of the form (subject, relation, object) where subject and objects are entities. For instance, the fact extractor can be used on the textual data of interest to generate the textual facts. The textual facts are in a triple data structure. The triple data structure comprises a subject, a relation, and an object. The subject and object are entities.

3. Setting up a reference KG that consists of a set of entities, a set of relations and a set of facts. The reference KG may contain just empty sets for starters if there is no other material available.

4. Create an enriched KG via: For each triple and each element in the triple:

a. Rank against entities/relations in reference KG. For instance, the textual facts are ranked. The textual facts are in a triple data structure comprising a subject, a relation, and an object.

b. Decide if element should be linked to an existing KG entity/relation or if it should become a new entity/relation. For instance, the fact linker 206 determines whether each element of the triple data structure (e.g., the subject, the relation, or the object) of the textual facts should be linked to an existing entry (e.g., an existing subject, relation, or object) within the reference KG or whether the element should become a new entry within the data element.

5. Give the enriched KG from 4) to a KG predictor 216 to derive the final outcome. For instance, for the robust drug development embodiment above, the final outcome can be information about using a particular drug to treat a particular treatment. In other words, the KG predictor 216 can perform predictions of the following form: (subject, relation,?), (?, relation, object), and/or (subject,?, object). If, for example, the KG predictor 216 gets an input (antimalarial; is used to treat;?), the KG predictor 216 can determine the output (e.g., final outcome) as "malaria".

Embodiments of the present invention provide advantages in contrast to existing technology. For instance, the problem of linking textual facts to Knowledge Graphs is related to both entity linking and relation inference problems. Current entity linking methods, however, are unable to link relation to knowledge graphs, and it is unclear how they deal with scenarios whether the link is polysemous, e.g., entity span which might refer to multiple KG entities. For instance, compared to prior art entity linkers such as (BLINK [see, e.g., Ledell Wu, Fabio Petroni, Martin Josifoski, Sebastian Riedel, Luke Zettlemoyer: "Scalable Zero-shot Entity Linking with Dense Entity Retrieval", @ EMNLP, 2020, the entire contents of which, are hereby incorporated by reference herein], GENRE [see, e.g., Nicola De Cao, Gautier Izacard, Sebastian Riedel, Fabio Petroni: "Autoregressive Entity Retrieval", ICLR, 2021, the entire contents of which, are hereby incorporated by reference herein]), embodiments of the present invention can link both entities and relations to a large scale KG, and implement a tailor-made module for dealing with polysemous entities (e.g. aggregation of the graph-based entity embeddings). Other approaches (OpenKI [see, e.g., Dongxu Zhang, Subhabrata Mukherjee, Colin Lockard, Xin Luna Dong, Andrew McCallum: "OpenKI: Integrating Open Information Extraction and Knowledge Bases with Relation Inference", NAACL-HLT (1) 2019: 762-772, the entire contents of which, are hereby incorporated by reference herein], CORI [see e.g., Zhengbao Jiang, Jialong Han, Bunyamin Sisman, Xin Luna Dong: "CoRI: Collective Relation Integration with Data Augmentation for Open Information Extraction", ACL/IJCNLP (1) 2021: 4706-4716, the entire contents of which, are hereby incorporated by reference herein]) perform linking of the textual fact's relation to a Knowledge Graph relation, but require to make the assumption that the entities are linked a priori, which is not the case in practice.

Figure 5:
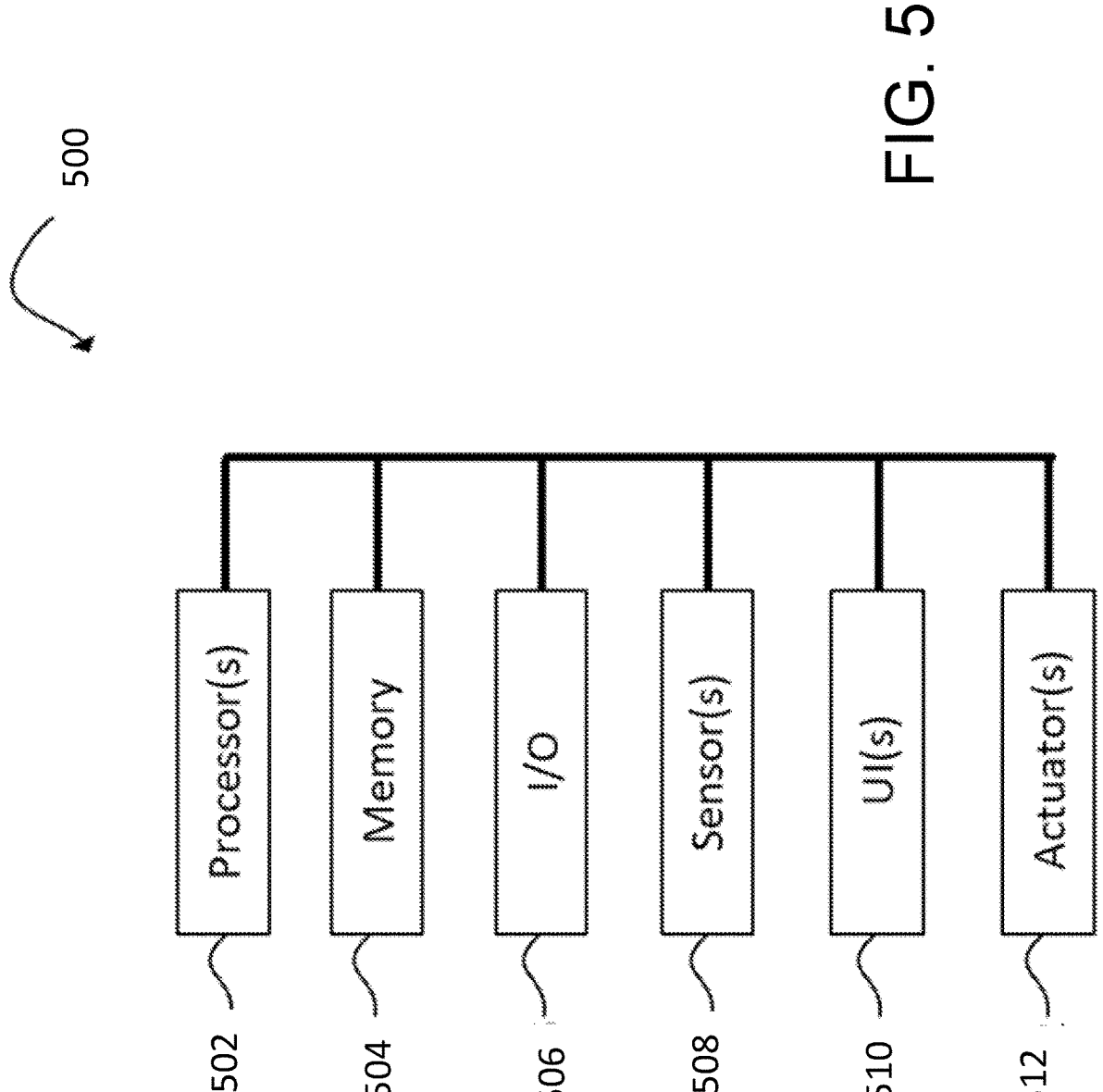
FIG. 5 is a block diagram of an exemplary processing system, which can be configured to perform any and all operations disclosed herein.

FIG. 5 is a block diagram of an exemplary processing system, which can be configured to perform any and all operations disclosed herein. Referring to FIG. 5, a processing system 500 can include one or more processors 502, memory 504, one or more input/output devices 506, one or more sensors 508, one or more user interfaces 510, and one or more actuators 512. Processing system 500 can be representative of each computing system disclosed herein.

Processors 502 can include one or more distinct processors, each having one or more cores. Each of the distinct processors can have the same or different structure. Processors 502 can include one or more central processing units (CPUs), one or more graphics processing units (GPUs), circuitry (e.g., application specific integrated circuits (ASICs)), digital signal processors (DSPs), and the like. Processors 502 can be mounted to a common substrate or to multiple different substrates.

Processors 502 are configured to perform a certain function, method, or operation (e.g., are configured to provide for performance of a function, method, or operation) at least when one of the one or more of the distinct processors is capable of performing operations embodying the function, method, or operation. Processors 502 can perform operations embodying the function, method, or operation by, for example, executing code (e.g., interpreting scripts) stored on memory 504 and/or trafficking data through one or more ASICs. Processors 502, and thus processing system 500, can be configured to perform, automatically, any and all functions, methods, and operations disclosed herein. Therefore, processing system 500 can be configured to implement any of (e.g., all of) the protocols, devices, mechanisms, systems, and methods described herein.

For example, when the present disclosure states that a method or device performs task "X" (or that task "X" is performed), such a statement should be understood to disclose that processing system 500 can be configured to perform task "X". Processing system 500 is configured to perform a function, method, or operation at least when processors 502 are configured to do the same.

Memory 504 can include volatile memory, non-volatile memory, and any other medium capable of storing data. Each of the volatile memory, non-volatile memory, and any other type of memory can include multiple different memory devices, located at multiple distinct locations and each having a different structure. Memory 504 can include remotely hosted (e.g., cloud) storage.

Examples of memory 504 include a non-transitory computer-readable media such as RAM, ROM, flash memory, EEPROM, any kind of optical storage disk such as a DVD, a Blu-Ray® disc, magnetic storage, holographic storage, a HDD, a SSD, any medium that can be used to store program code in the form of instructions or data structures, and the like. Any and all of the methods, functions, and operations described herein can be fully embodied in the form of tangible and/or non-transitory machine-readable code (e.g., interpretable scripts) saved in memory 504.

Input-output devices 506 can include any component for trafficking data such as ports, antennas (i.e., transceivers), printed conductive paths, and the like. Input-output devices 506 can enable wired communication via USB®, DisplayPort®, HDMI®, Ethernet, and the like. Input-output devices 506 can enable electronic, optical, magnetic, and holographic, communication with suitable memory 506. Input-output devices 506 can enable wireless communication via WiFi®, Bluetooth®, cellular (e.g., LTE®, CDMA®, GSM®, WiMax®, NFC®), GPS, and the like. Input-output devices 306 can include wired and/or wireless communication pathways.

Sensors 508 can capture physical measurements of environment and report the same to processors 502. User interface 510 can include displays, physical buttons, speakers, microphones, keyboards, and the like. Actuators 512 can enable processors 502 to control mechanical forces.

Processing system 500 can be distributed. For example, some components of processing system 500 can reside in a remote hosted network service (e.g., a cloud computing environment) while other components of processing system 500 can reside in a local computing system. Processing system 500 can have a modular design where certain modules include a plurality of the features/functions shown in FIG. 5. For example, I/O modules can include volatile memory and one or more processors. As another example, individual processor modules can include read-only-memory and/or local caches.

The following is also incorporated by reference herein in its entirety: Jeff Johnson, Matthijs Douze, Hervé Jégou: "Billion-Scale Similarity Search with GPUs", IEEE Trans. Big Data 7 (3): 535-547, 2021.

While embodiments of the invention have been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A method for disambiguating textual facts by linking the textual facts to a reference knowledge graph and introducing entities and relations for the textual facts, comprising:

determining textual fact embeddings for the textual facts from textual data based on using a first pre-trained language model (LM), wherein each of the textual facts is in a triple data structure comprising a plurality of elements, wherein each of the plurality of elements is a subject, a relation, or an object;

determining one or more knowledge graph entities and relation embedding vectors using frozen knowledge graph embeddings;

determining one or more intermediate knowledge graph embeddings using a second pre-trained LM;

determining knowledge graph embeddings based on using an aggregator, the one or more knowledge graph entities and relation embedding vectors, and the one or more intermediate knowledge graph embeddings;

ranking the textual facts based on the knowledge graph embeddings and the textual fact embeddings;

based on the ranking, determining first outputs indicating that a first subset of the plurality of elements should be linked to an existing entry within the reference knowledge graph and second outputs indicating that a second subset of the plurality of elements should be added as a new entry within the reference knowledge graph; and generating an enriched knowledge graph based on the first outputs and the second outputs.

2. The method of claim 1, further comprising:

obtaining the textual data of interest; and using a fact extractor on the textual data of interest to generate the textual facts, and wherein the subject and the object are entities.

3. The method of claim 1, further comprising:

setting up the reference knowledge graph comprising a set of entities, a set of relations, and a set of knowledge graph facts.

4. The method of claim 3, wherein the reference knowledge graph starts with empty sets for the set of entities, the set of relations, and the set of knowledge graph facts.

5. The method of claim 3, wherein setting up the reference knowledge graph comprises:

determining whether one or more previous facts from previous textual data exists in the reference knowledge graph; and based on determining that the one or more previous facts does not exist in the reference knowledge graph, adding new entity and relations associated with the one or more previous facts as well as the one or more previous facts into the reference knowledge graph.

6. The method of claim 1, further comprising:

inputting the enriched knowledge graph into a knowledge graph predictor to determine a final outcome.

7. The method of claim 6, wherein the textual data indicates textbooks and publications, and wherein the final outcome indicates information associated with using a particular drug to treat a particular patient.

8. The method of claim 6, wherein the textual data indicates facility reports and/or logs indicating stored items in a facility, and wherein the final outcome indicates linked facts indicating items and robots in an inventory and locations of the items and the robots within the facility, and wherein the method further comprising:

operating an artificial intelligence (AI) system to command the robots in the facility to move the items to a proper location based on the final outcome.

9. The method of claim 1, wherein ranking the textual facts based on the knowledge graph embeddings and the textual fact embeddings comprises using a shared latent space between the knowledge graph embeddings and the textual fact embeddings to rank the textual facts.

10. The method of claim 1, wherein determining the first outputs and the second outputs comprises:

generating one or more aggregated feature vectors for each of the textual facts;

determining the first outputs and the second outputs based on the one or more aggregated feature vectors, wherein each of the first outputs and the second outputs comprises a plurality of probability scores associated with the plurality of elements of the textual facts; and determining whether each element from the plurality of elements should be linked to the existing entry within the reference knowledge graph or added as the new entry within the reference knowledge graph is based on comparing the plurality of probability scores with a threshold.

11. The method of claim 10, wherein the one or more aggregated feature vectors comprise a ranking score, a previous link, a current link, a current link additional information, and a closest text, and wherein determining the plurality of probability scores is based on using a softmax layer in a neural network.

12. A system for disambiguating textual facts by linking the textual facts to a reference knowledge graph and introducing entities and relations for the textual facts, the system comprising one or more hardware processors, which, alone or in combination, are configured to provide for execution of the following steps:

determining textual fact embeddings for the textual facts from textual data based on using a first pre-trained language model (LM), wherein each of the textual facts is in a triple data structure comprising a plurality of elements, wherein each of the plurality of elements is a subject, a relation, or an object;

determining one or more knowledge graph entities and relation embedding vectors using frozen knowledge graph embeddings;

determining one or more intermediate knowledge graph embeddings using a second pre-trained LM;

determining knowledge graph embeddings based on using an aggregator, the one or more knowledge graph entities and relation embedding vectors, and the one or more intermediate knowledge graph embeddings;

ranking the textual facts based on the knowledge graph embeddings and the textual fact embeddings;

based on the ranking, determining first outputs indicating that a first subset of the plurality of elements should be linked to an existing entry within the reference knowledge graph and second outputs indicating that a second subset of the plurality of elements should be added as a new entry within the reference knowledge graph; and generating an enriched knowledge graph based on the first outputs and the second outputs.

13. A tangible, non-transitory computer-readable medium having instructions thereon which, upon being executed by one or more processors, alone or in combination, provide for execution of a method for disambiguating textual facts by linking the textual facts to a reference knowledge graph and introducing entities and relations for the textual facts comprising the following steps:

determining textual fact embeddings for the textual facts from textual data based on using a first pre-trained language model (LM), wherein each of the textual facts is in a triple data structure comprising a plurality of elements, wherein each of the plurality of elements is a subject, a relation, or an object;

determining one or more knowledge graph entities and relation embedding vectors using frozen knowledge graph embeddings;

determining one or more intermediate knowledge graph embeddings using a second pre-trained LM;

determining knowledge graph embeddings based on using an aggregator, the one or more knowledge graph entities and relation embedding vectors, and the one or more intermediate knowledge graph embeddings;

ranking the textual facts based on the knowledge graph embeddings and the textual fact embeddings;

based on the ranking, determining first outputs indicating that a first subset of the plurality of elements should be linked to an existing entry within the reference knowledge graph and second outputs indicating that a second subset of the plurality of elements should be added as a new entry within the reference knowledge graph; and generating an enriched knowledge graph based on the first outputs and the second outputs.

14. The method of claim 1, wherein determining the first outputs and the second outputs comprises:

building a plurality of feature vectors based on the ranking, wherein each of the plurality of feature vectors is associated with an element from the plurality of elements; and generating the first outputs and the second outputs based on the plurality of feature vectors and using a binary classifier.

15. The method of claim 14, wherein the plurality of feature vectors comprises a first feature vector associated with a link between the existing entry within the reference knowledge graph and a first element from the plurality of elements for a first textual fact from the textual facts.

16. The method of claim 15, wherein generating the first outputs comprises:

processing the first feature vector using a softmax layer to generate a score for the first feature vector; and performing binary classification using the binary classifier by comparing the score generated using the softmax layer with a threshold to determine that the first element for the first textual fact is to be linked to the existing entry within the reference knowledge graph.

17. The method of claim 15, wherein generating the second outputs comprises:

processing the first feature vector and additional feature vectors for the first element using a softmax layer to generate a plurality of scores for the element;

performing binary classification using the binary classifier by comparing the plurality of scores generated using the softmax layer with a threshold to determine that the first element should be added as the new entry within the reference knowledge graph.

* * * * *